US005789538A

United States Patent [19]
Rebar et al.

[11] Patent Number: 5,789,538
[45] Date of Patent: Aug. 4, 1998

[54] ZINC FINGER PROTEINS WITH HIGH AFFINITY NEW DNA BINDING SPECIFICITIES

[75] Inventors: Edward J. Rebar, Cambridge; Carl O. Pabo, Newton, both of Mass.

[73] Assignee: Massachusetts Institute of Technology, Cambridge, Mass.

[21] Appl. No.: 850,250

[22] Filed: Apr. 18, 1997

Related U.S. Application Data

[63] Continuation of Ser. No. 383,056, Feb. 3, 1995, abandoned.
[51] Int. Cl.$^6$ .................... C07K 14/00; C07K 14/435; C07K 14/46; C07K 14/82
[52] U.S. Cl. .................. 530/324; 530/300; 530/350; 530/358; 530/400
[58] Field of Search ................... 530/300, 324, 530/350, 358, 400; 435/69.1, 172.3

[56] References Cited

U.S. PATENT DOCUMENTS

| | | | |
|---|---|---|---|
| 5,096,815 | 3/1992 | Ladner et al. | 435/69.1 |
| 5,223,409 | 6/1993 | Ladner et al. | 435/69.7 |

FOREIGN PATENT DOCUMENTS

WO95/19431   7/1995   WIPO.

OTHER PUBLICATIONS

International Search Report for (AL) WO95/19431.
Thiesen, H. J. and Bach, C., "Determination of DNA Binding Specificities of Mutated Zinc Finger Domains," *Federatioin of European Biochemical Societies*, 283(1):23–26 (1991).
Nardelli, J., et al., "Zinc Finger–DNA Recognition: Analysis of Base Specificity by Site–Directed Mutagenesis," *Nucleic Acids Research*, 20(16):4137–4144 (1992).
Desjarlais, J. R. and Berg, J. M., "Redesigning the DNA-Binding Specificity of a Zinc Finger Protein: A Data Base–Guided Approach," *PROTEINS: Structure, Function and Genetics*, 12:101–104 (1992).
Desjarlais, J. R. and Berg, J. M., "Toward Rules Relating Zinc Finger Protein Sequences and DNA Binding Site Preferences," *Proc. Natl. Acad. Aci. USA*, 89:7345–7349 (Aug. 1992).
Desjarlais, J. R. and Berg, J. M., "Use of a Zinc–Finger Consensus Sequence Framework and Specificity Rules to Design Specific DNA Binding Proteins," *Proc. Natl. Acad. Aci. USA*, 90:2256–2260 (Mar. 1993).
Jamieson, A. C., et al., "In Vitro Selection of Zinc Fingers with Altered DNA–Binding Specificity," *Biochemistry*, 33:5689–5695 (1994).
Choo, Y. and Klug A., "Toward a Code for the Interactions of Zinc Fingers with DNA: Selection of Randomized Fingers Displayed on Phage," *Proc. Natl. Acad. Sci. USA*, 91:11163–11167 (1994).
Choo Y. and Klug A., "Selection of DNA Binding Sites for Zinc Fingers Using Rationally Randomized DNA Reveals Coded Interactions," *Proc. Natl. Acad. Sci. USA*, 91:11168–11172 (1994).
Wu, H., et al., "Building Zinc Fingers by Selection: Toward a Therapeutic Application," *Proc. Natl. Acad. Sci. USA*, 92:344–348 (1995).
Choo, Y., et al., "In Vivo Repression by a Site–Speicific DNA–Binding Protein Designed Against an Oncogenic Sequence," *Nature*, 372:642–645 (1994).
Rice, W. G. et al. *Science* 270:1194–1197 (1995).
Taylor, W. E. et al. *Biochemistry* 34:3222–3230 (1995).

*Primary Examiner*—Dian C. Jacobson
*Attorney, Agent, or Firm*—Hamilton, Brook, Smith & Reynolds, P.C.

[57] ABSTRACT

Described is a polypeptide comprising one or more zinc fingers. The polypeptide binds to new polynucleotide subsites with high affinity and consequently has a binding specificity that differs from wild type zinc finger proteins. The binding occurs through contacts between certain amino acid residues of the zinc fingers and the nucleic acids of the subsites. The polypeptide sequence of at least one zinc finger differs from wild type zinc fingers, and the difference involves at least one amino acid residue that contacts the bases of the polynucleotide during binding.

8 Claims, 3 Drawing Sheets

```
             GACC
             GCAC
             CCTG
CTGA GCGTGG____ AGTGATCGATC-biotin
GACT CGCACCxxxx TCAC
```

Fig. 3

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:1:

TCGATCAGGG CCCTTCGAAA CTAGTGCACC TGCAGAGGAT CCT    43

( 2 ) INFORMATION FOR SEQ ID NO:2:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:2:

TCGAAAGATC CTCTGCAGGT GCACTAGTTT CGAAGGGCCC TGA    43

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:3:

CTGAGCGTGG NNNNAGTGAT CGATC    25

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:4:

CACTNNNNCC ACGCTCAG    18

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: unknown ( x i ) SEQUENCE DESCRIPTION: SEQ ID NO:5:

```
AGCAGCTGAG CGTCCNNNNA GTGAGCT                                               27
```

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: unknown ( x i ) SEQUENCE DESCRIPTION: SEQ ID NO:6:

```
ATGCTGCATA TAAGCAGCTG CTT                                                   23
```

( 2 ) INFORMATION FOR SEQ ID NO:7:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:7:

```
GGAATCGATT CCATGGGCC CCATGAACGG CCGTACGCCT TGCCCTGTCG AGTCCTGCGA            60

TCGTCGATTT TCG                                                              73
```

( 2 ) INFORMATION FOR SEQ ID NO:8:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: unknown ( x i ) SEQUENCE DESCRIPTION: SEQ ID NO:8:

```
CCATCTCGAT CGCATGCATA TTCGACACTG GAAGGGCTTC TGGCCTGTGT GGATCCGGAT           60

ATGSNNGGTG AGSNNSNNAG ASNNCGAAAA TCGACG                                     96
```

( 2 ) INFORMATION FOR SEQ ID NO:9:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

```
GCGTGGGCG                                                                   9
```

ZINC FINGER PROTEINS WITH HIGH AFFINITY NEW DNA BINDING SPECIFICITIES

RELATED APPLICATION

This application is a continuation of application Ser. No. 08/383,056 filed on Feb. 3, 1995, now abandoned which is incorporated herein by reference in its entirety.

BACKGROUND OF THE INVENTION

There are many diseases which are caused by the overexpression of certain genes. For example, replication of viruses such as human immunodeficiency virus (HIV) are facilitated by the expression of certain viral genes by host cells. Many cancers are caused by the overexpression of certain genes, referred to as oncogenes. Such viral infection could be treated and the growth of such tumors could be prevented if the expression of the genes could be suppressed. Proteins which bind to the promoter sites of these genes would prevent their expression. However, there exists a need for proteins which can bind to the specific polynucleotide sequences of these promoter regions and which can be targeted to the cells which are overexpressing the undesired proteins.

SUMMARY OF THE INVENTION

The present invention is a polypeptide having three or more zinc fingers. The polypeptide binds specifically to a unique DNA site with high affinity. Zinc fingers typically bind to a span of three to four polynucleotide base pairs, referred to as a "subsite".

Another embodiment is a deoxyribonucleic acid that comprises a gene which encodes for the polypeptide of the present invention.

In the present invention, the polypeptide encompassing the zinc fingers 1) differs in sequence—at one or more base-contacting amino acid residues—from a known wild type zinc finger protein or has a base sequence specificity distinct from that of a known wild type zinc finger protein and 2) binds to a targeted polynucleotide with high affinity (binds DNA with high affinity, i.e., with a dissociation constant of less than 1 nanomolar (nM)). In one embodiment, a polypeptide of the present invention differs in the identity of its base-contacting amino acid residues from a corresponding wild type zinc finger protein, such as Zif268. In another embodiment, the polypeptide has a DNA binding specificity different from that of any known zinc finger protein. The base sequence specificity of a protein can be determined by selecting the optimal binding site from a pool of duplex DNA with random sequence.

The polypeptide of the present invention has many uses. It can be used in research or in treatment to alter the expression of certain proteins by binding to the transcription control element of the protein. For example, when directed to a suitable target site in a human or animal, the polypeptide can be used to suppress the expression of a protein involved in a disease process, e.g. a viral protein or an oncogene. A zinc finger protein with high affinity and new DNA binding specificity can be used to enhance gene expression. In research, the polypeptide, when combined with a suitable label (e.g. a radioactive or fluorescent label) can be used to identify a unique polynucleotide sequence within a larger polypeptide by binding to the unique sequence.

BRIEF DESCRIPTION OF THE DRAWINGS

FIG. 3 shows the three biotinylated DNA sites used for affinity selections (SEQ ID NO. 3) and the complementary strands (SEQ. ID NO. 4). The sequences of the underscored region were GACC, GCAC, or CCTG (where XXXX indicates the appropriate complementary sequence), and these duplexes are referred to as GACC, GCAC, and CCTG. Zif normally recognizes duplex DNA with the consensus sequence GCGTGGGCG (with the first finger contacting the underlined "GCG" subsite) and the box marks the corresponding regions of the duplexes.

DETAILED DESCRIPTION OF THE INVENTION

Figure 1:
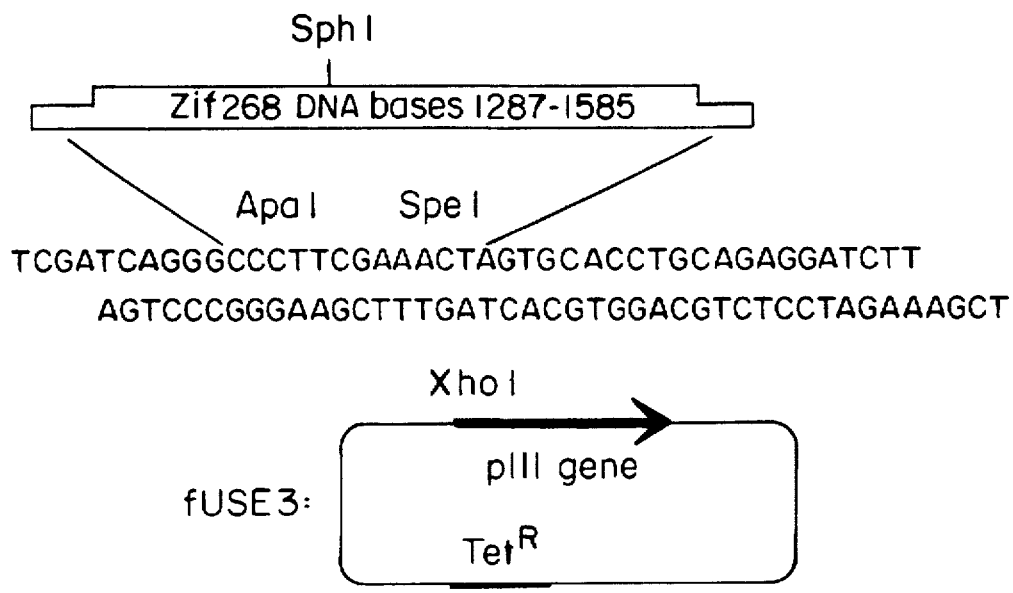
FIG. 1 is the construction of the Zif phage vector fd-tet.Zif. The phage vector fUSE3 was converted into fd-tet.Zif in two steps: (i) a polylinker was inserted into the Xho I site of fUSE3 and (ii) a PCR-amplified fragment of Zif268 complementary DNA (the upper strand is SEQ. ID NO. 1 and the lower strand is SEQ. ID NO. 2) encompassing bases 1287 through 1585 was cut with Apa I and Xba I and then ligated into the Apa I and Spe I sites of the polylinker.

One embodiment of the present invention is a polypeptide that binds a targeted polynucleotide with high affinity. "High affinity" means that the polypeptide binds the targeted polynucleotide with a dissociation constant [$K_d$] of less than about 1.0 nanomolar, preferably less than about 0.5 nanomolar. The polypeptide comprises three or more zinc fingers. The binding of the polypeptide to the target polynucleotide is brought about through contacts between amino acid residues of the zinc fingers and the nucleic acid bases of the polynucleotide, thereby forming a stable polynucleotide/polypeptide complex. In the present invention, the polypeptide encompassing the zinc fingers 1) differs in sequence—at one or more base-contacting amino acid residues—from a known wild type zinc finger protein or has a base sequence specificity distinct from that of a known wild type zinc finger protein and 2) binds to a targeted polynucleotide with high affinity (binds DNA with high affinity, i.e., with a dissociation constant of less than 1 nM). In one embodiment, a polypeptide of the present invention differs in the identity of its base—contacting amino acid residues from a corresponding wild type zinc finger protein, such as Zif268. In another embodiment, the polypeptide has a DNA binding specificity different from that of any known zinc finger protein. The base sequence specificity of a protein can be determined by selecting the optimal binding site from a pool of duplex DNA with random sequence.

Zinc fingers are involved in eukaryotic protein-nucleic acid interactions that control gene transcription. Naturally occurring zinc fingers, referred to herein as "wild type" zinc fingers occur in regulatory fractions that include differentiation and growth signals [EGR1, also referred to as Zif268, (Sukhatme, V. P. et al., *Cell*, 53:37 (1988); Christy, B. A., et al., *Proc. Natl. Acad. Sci. U.S.A.*, 85:7857 (1988)), EGR2 (Joseph, L. J., et al., *Proc. Natl. Acad. Sci. U.S.A.*, 85:7164 (1988); Chavrier, P. et al., *EMBO J.* 7:29 (1988))], in protooncogenes [GLI (Kinzler, K. W., et al., *Nature*, 332:371 (1988)), Wilm's tumor gene (Call, K. M. et al., *Cell*, 60:509 (1990))], in general transcription factors [SP1 (Gidoni, D., et al., *Nature*, 312:409 (1984))], in Drosophila segmentation genes [Hunchback (Tautz, D., et al., *Nature*, 327:383 (1987)), Kruppel (Rosenberg, U. B., et al., *Nature*, 319:336 (1986))], and in regulatory genes of lower eukaryotic organisms [ADR1 (Bermis, L. T., and Denis, C. L., *Mol. Cell. Biol.*, 8:2125 (1988)), BrLA (Adams, T. H., et al., *Cell*, 54:353 (1988))].

As used herein, a zinc finger is a polypeptide structural motif folded around a bound zinc cation. The polypeptide of a zinc finger has a sequence of the form $X_3$-Cys-$X_{2-4}$-Cys-$X_{12}$-His-$X_{3-5}$-His-$X_4$, wherein X is any amino acid (e.g. $X_{2-4}$ indicates an oligopeptide 2–4 amino acids in length). There is generally a wide range of sequence variation in the 28–31 amino acids of the known zinc finger polypeptide. Only the two consensus histidine residues and two consensus cysteine residues bound to the central zinc atom are invariant. Of the remaining residues, three to five are highly conserved, while there is significant variation among the other residues. Despite the wide range of sequence variation in the polypeptide, zinc fingers of this type have a similar three dimensional structure. However, there is a wide range of binding specificities among the different zinc fingers, i.e. different zinc fingers bind double stranded polynucleotides having a wide range of nucleotides sequences.

The binding specificity and affinity of a zinc finger is largely determined to a large degree by the amino acid residues which contact the nucleic acids of the polynucleotide. Based on the three published reports of the x-ray crystal structures of zinc fingers complexed to DNA (Pavletich and Pabo, *Science* 252:809 (1991), Pavletich and Pabo, *Science* 261:1701 (1993) and Fariall et al., *Nature* 366:483 (1993)), there are four nucleic acid-contacting residues in zinc fingers that are primarily responsible for determining specificity and affinity. These four amino acid residues occur in the same position relative to the first consensus histidine and the second consensus cysteine. Specifically, these four amino acid residues define which three to four base pair [or subsites] the zinc finger prefers to bind (i.e. the specificity of the zinc finger) and with how great an affinity. The first of the three critical amino acid residues is seven residues to the N-terminal side of the first consensus histidine and six residues to the C-terminal side of the second consensus cysteine. This is hereinafter referred to as the "−1 position". The other three amino acids are two, three and six residues removed from the C-terminus of the residue at position −1, and are referred to as the "2 position", "3 position" and "6 position", respectively. The amino acid residues one and five residues removed from the C-terminus of the amino acid at the −1 position are also important to zinc finger specificity and binding strength. Positions one and five residues removed from the C-terminus of the amino acid at −1 are referred to as the "1 position" and "5 position", respectively. These amino acid residues at these six positions are referred to as the base-contacting amino acids. These six positions are referred to as "base contacting positions." It is to be understood that in a given zinc finger protein, not all of the amino acids at these six positions contact the double stranded DNA.

As used herein, a "targeted polynucleotide" refers to a portion of double-stranded polynucleotide acid (e.g. RNA, DNA, PNA or combinations thereof) to which it is advantageous to bind a protein. In addition, a "targeted polynucleotide" binds wild type zinc protein with low affinity, i.e., with a binding constant greater than about 1.0 nanomolar under conditions described in Example 6. In one aspect, a "targeted polynucleotide" will be all or part of a transcriptional control element for a gene for which a desirable result can be attained by altering the degree of its expression. A transcriptional control element includes positive and negative control elements such as a promoter, an enhancer, other response elements (e.g. steroid response element, heat shock response element or metal response element) a repressor binding sites, operator and/or silencers. The transcriptional control element can be viral (e.g. the HIV promoter or the adenovirus promoter), eukaryotic (e.g., the p53 oncogene promoter) or prokaryotic. A "targeted polynucleotide" can also refer to a downstream sequence which could bind a protein and thereby prevent transcription.

For example, it is desirable to decrease the expression of oncogenes (such as mutant formed of p53) in cancer patients or certain viral genes (e.g. certain HIV or adenovirus genes) in virus-infected individuals. A protein containing zinc fingers which binds to these transcription control elements on other sites in the promoter region will cause a decrease in the expression of these genes by blocking the binding of transcription factors that normally stimulate gene expression. Consequently, the polypeptides of the present invention can be used in gene therapy. In other instances, it may be desirable to increase expression of a particular protein such as a lipoprotein receptor involved in cholesterol metabolism. A zinc protein which binds to the promoter site of the protein and which contains a transcription activator can cause such an increase in expression. In other instances, it may be desirable to attach another protein, for example a nuclease, to a zinc finger protein which binds to a double stranded polynucleotide having a particular sequence. In this case, the DNA in the vicinity of the site to which the zinc finger attaches would be degraded by the nuclease. Such a protein complex would be useful for destroying certain undesirable cells, for example cancer cells. Fragments produced by such nuclease/zinc finger complex would be useful for gene mapping and for cloning.

In another aspect, a "targeted polynucleotide" is a short portion of duplex nucleic acid (e.g. RNA, DNA, PNA or any hybrids thereof) having from about 8 to about 40 base pairs) having a defined sequence for which there is some desirable purpose in determining its presence or absence within a larger polynucleotide. For example, it may be desirable to determine whether a particular promoter or control region is found within the genome of a particular organism. A labeled protein (e.g. bound with a radioactive or fluorescent label) containing zinc fingers which binds to a polynucleotide having this particular sequence can be used to determine whether the genetic material of the organism contains this particular sequence.

When a multifinger protein binds to a polynucleotide duplex (e.g. DNA, RNA, PNA or any hybrids thereof) its fingers typically line up along the polynucleotide duplex with a periodicity of about one finger/3 bases of polynucleotide. The binding sites of individual zinc fingers (or subsites), however, typically span three to four bases, and so subsites of adjacent fingers usually overlap by one base. For example, binding of three-finger protein 123 to the 10 base pair site ABCDEFGHIJ (where these letters indicate one of the duplex DNA) could be 3 2 1 represented as ABCDEFGHIJ with the subsite of finger 1 being GHIJ, finger 2 being DEFG and finger 3 being ABCD. To design a three-finger protein to bind to the targeted 10 base site ABCDEFXXXX (wherein each "X" represents a base that would be specified in a particular application), zinc fingers 2 and 3 would have the same polypeptide sequence as found in wild type zinc fingers which bind DEFG and ABCD, respectively. Finger 1 would have a mutated polypeptide sequence. Preferably, finger 1 would have mutations at one or more of the base-contacting positions, i.e. finger 1 would have the same polypeptide sequence as a wild type zinc finger except that at least one of the four amino residues at the primary positions would differ. Similarly, to design a three-finger zinc protein that would bind to a 10 base sequence ABCXXXXHIJ (wherein each "X" is base that would be specified in a particular application), fingers 1 and 3 have the same sequence as the wild type zinc fingers which bind GHIJ and ABCD, respectively, while finger 2 would have residues at one or more base-coating positions which differ from those in a wild type finger. The present invention encompasses multifingered proteins in which more than one finger differs from a wild type zinc finger. It also includes multifingered protein in which the amino acid sequence in all the fingers have been changed.

It is also possible to design or select a zinc finger protein to bind to a targeted polynucleotide in which more than four bases have been altered. In this case, more than one finger of the binding protein must be altered. For example, in the 10 base sequence XXXDEFGXXX, a three-finger binding protein could be designed in which fingers 1 and 3 differ from the corresponding fingers in a wild type zinc finger, while finger 2 will have the same polypeptide sequence as the corresponding finger in the wild type fingers which binds to the subsite DEFG. Binding proteins having more than three fingers can be also designed for base sequences of longer length. For example, a four finger-protein will optimally bind to a 13 base sequence, while a five-finger protein will optimally bind to a 16 base sequence. A multifinger protein can also be designed in which some of the fingers are not involved in binding to the selected DNA, and the GLI-DNA complex also shows that slight variations are possible in the spacing of the fingers.

Another embodiment of the present invention is a deoxyribonucleotide which encodes a polypeptide that binds a targeted polynucleotide with high affinity (as described above). The polypeptide comprises three or more zinc fingers. The binding of the polypeptide to the targeted polynucleotide duplex is brought about through contacts between amino acid residues of the zinc fingers and the nucleic acid bases of the targeted polynucleotide, thereby forming the duplex polynucleotide/polypeptide complex. At least one base-contacting amino acid residue in at least one zinc finger differs from the amino acid in the corresponding position in the wild type zinc finger, i.e. the polypeptide of the present invention differs from wild type zinc finger proteins in the amino residues present in at least one amino acid residue which contacts the target polynucleotide.

In a preferred embodiment, one or more amino acids in one or more zinc fingers of the polypeptide are mutated in the base-contacting positions. Examples of suitable targeted a promoter region polynucleotides include a transcription control element or promoter region, as described above. Suitable wild type zinc fingers include EGR1, EGR2, GLI, Wilson's tumor gene, Sp1, Hunchback, Kruppel, ADR1 and BrLA.

A phage display system was developed and used to select zinc finger proteins with altered DNA-binding specificities.

Figure 2:
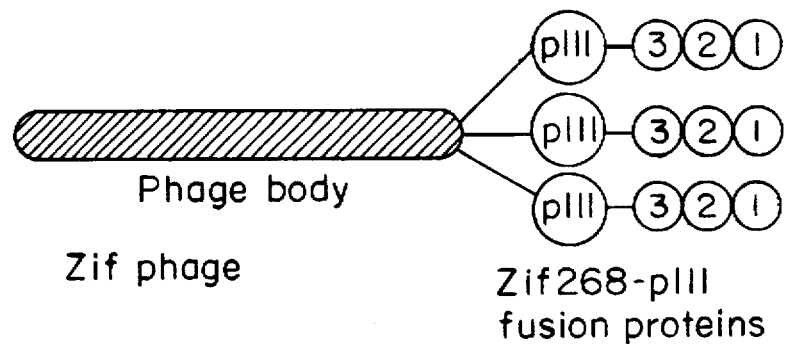
FIG. 2 is a sketch of the Zif phage. The Zif268 zinc finger peptide, which contains three fingers (denoted by the numbered circles), is fused to the NH$_2$-terminal end of the phage coat protein pIII. Three to five copies of this fusion protein should be present at one end of the virion.

The three zinc fingers of the Zif268 protein were expressed on the surface of filamentous phage, and a library of variants was prepared by randomizing critical amino acids in the first zinc finger. Affinity selections, using DNA sites with base changes in the region recognized by the first finger, yielded Zif268 variants that bound tightly and specifically to the new sites. Three Zif268 zinc fingers (Christy, B. A., et al., *Proc. Natl. Acad. Sci. U.S.A.*, 85:7857 (1988)) were expressed on the surface of filamentous phage (FIGS. 1 and 2). The resulting construct-fd-tet.Zif-produced useful titers of "Zif phage" (Example 2), and these phage bound specifically to the nine-base pair site (GCGTGGGCG—the first finger contacts the underlined "GCG" subsite) recognized by Zif268. A library of Zif variants were created by randomizing the four positions of the first finger that appear most important for making base contacts (Pavletich, N. P. and Pabo, C. O., *Science*, 261:1701 (1993); Pavletich, N. P. and Pabo, C. O., *Science*, 252:809 (1991); Fairall, L., et al., *Nature*, 366:483 (1993)). These randomized positions include the residue immediately preceding the a helix and include the second, third, and sixth residues of the helix (Example 3). [Note: These correspond to positions −1, 2, 3 and 6 that were described previously.]

Affinity selection methods were then used to search the library for phage that would recognize altered binding sites. In each round of affinity selection, phage were equilibrated with biotinylated target DNA and then applied to streptavidin-coated microtiter wells. After washing, the retained phage were eluted in high salt buffer, amplified in *Escherichia coli*, and purified to prepare for the next cycle. The target DNA duplexes for these selections contained modified Zif268 binding sites with changes in the region recognized by finger one (Pavletich, N. P. and Pabo, C. O., *Science*, 252:809 (1991), and each duplex is referred to by the sequence of this region (FIG. 3). Initially, five rounds of selection were performed with each of the target sites (FIG. 4) (Example 4). During these initial selection series, retention efficiencies in the GACC- and GCAC-selected phage pools increased about 100 times, whereas retention efficiencies for the CCTG pool remained low (Example 5). These enriched GACC and GCAC were then used pools as a starting point for additional, more stringent selection cycles (FIG. 4) (14). The CCTG pool was not studied further.

Phage pools from critical stages of the GACC and GCAC selections were characterized by sequencing (FIG. 4), and amino acid preferences were apparent in each pool. For the GACC pool, sequencing after the initial selection series showed that all of the phage (12/12) could be characterized by the consensus sequence (S/D/T)_NR (Table 1). Three additional rounds of selection using high salt washes did not substantially change this consensus (Table 2). For the GCAC selections, sequencing revealed notable changes in the later pools. After the initial selection series, many of the phage belonged to a group characterized by the consensus sequence R_DR (18/22), but there also was a group characterized by the sequence _G(S/T)R (4/22) (Table 1). After additional rounds of selection with high salt washes, a single sequence RADR—from the first group predominated (Table 2). However, when the additional rounds of selection used both high salt washes and competitor Zif268 site in the binding reactions, a single sequence -QGSR- from the second group predominated.

TABLE 1

| GACC −1 2 3 6 | GCAC −1 2 3 6 |
|---|---|
| SQNR (4,2) | RSDR (4,2) |
| DANR (2,1) | RPDR (3,2) |
| DRNR | RGDR (3,1 |
| DSNR | HSDR (2,2) |
| SSNR | RVDR (2,2) |
| STNR | AADR |
| TANR | KSDR |
| TPNR | RADR |
|  | RAER |
|  | R_DR |
|  | NGSR (2,2) |
|  | SGST |
|  | TGTR |
| S/D/R_NR | _G S/T R |

Figure 4:
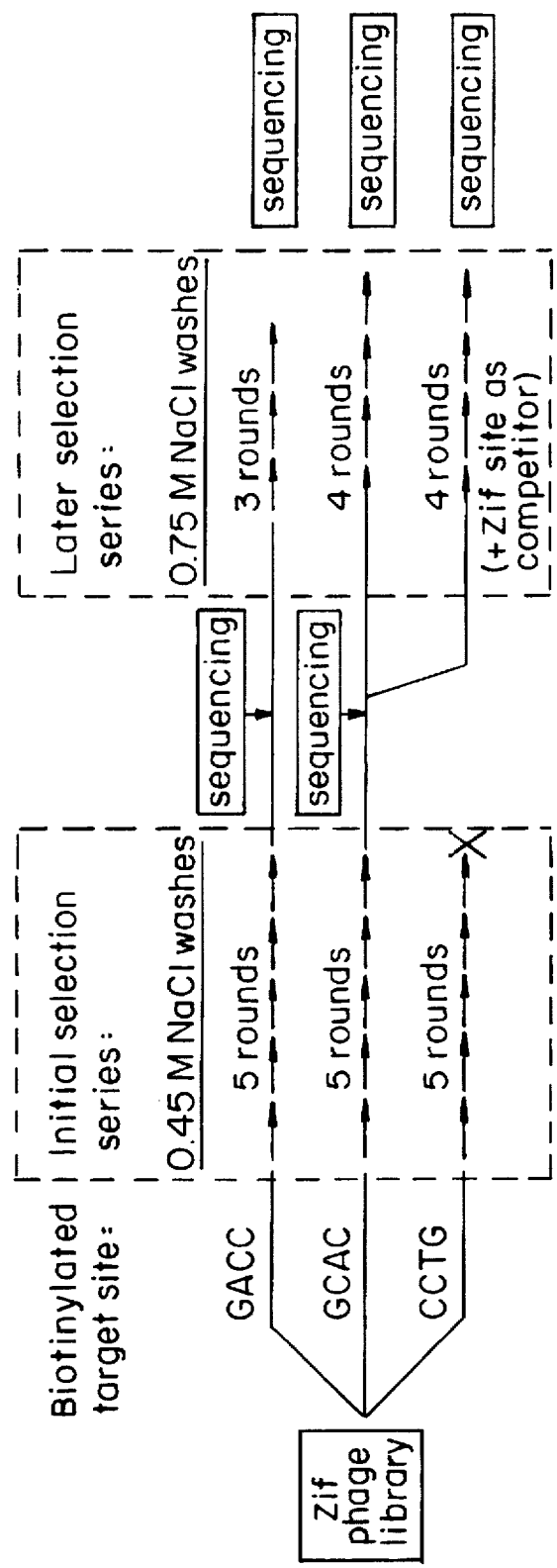
FIG. 4 is a overview of selections. Samples from the phage library were subjected to five rounds of selection with the biotinylated DNA duplexes GACC, GCAC, or CCTG. The GACC and GCAC pools were then used in additional rounds of selection under more stringent conditions (the washes contained more salt and, for one of the GCAC selections, the binding reactions contained nonbiotinylated Zif268 binding site as a specific competitor) (Example 4). Pools were characterized at the indicated stages by sequencing of randomly chosen phage. The X indicates that there were no further selections with the CCTG pool.

Amino Acid sequences of phage from the GACC and GCAC pools after the initial selection series (FIG. 4). The four randomized positions in the α-helical region of finger one are denoted as −1, 2, 3, and 6. Consensus sequences are indicated in bold. An underscore ( ) indicates that there is no clear preference at the corresponding position. The numbers in parentheses indicate the total number of times this amino acid sequence was recovered and the number of distinct DNA sequences that encoded this amino acid sequence. Single-letter abbreviations for the amino acid residues are as follows: A, Ala; D, Asp; E, Glu; G, Gly; H, His; K, Lys; N, Asn; P, Pro; Q, Gln; R, Arg; S, Ser; T, Thr; and V, Val.

TABLE 2

| GACC −1 2 3 6 | GCAC −1 2 3 6 | GCAC (+ competitor) −1 2 3 6 |
|---|---|---|
| DSNR (8,4) | RADR (7,4) | QGSR (16,3) |
| SSNR (4,3) |  |  |
| DRNR (2,1) |  |  |
| NSNR |  |  |
| D/S SNR | RADR | QGSR |

Amino acid sequences in the final phage pools (after the later selection series shown in FIG. 4). The designation "+ competitor" indicates that specific competitor DNA (nonbiotinylated wild-type Zif268 site) was added to the binding mixes during the later selection series (Example 4). Symbols are as described in Table 1.

Three Zif268 variants were studied in more detail by recloning and overexpressing then in *E. coli*, then purifying the resultant peptides and measuring DNA-binding affinities. Also studied were the predominant Zif268 variants obtained in each of the three later selection series—DSNR, RADR, and QGSR (Table 2)—and also included the wild-type peptide RDER as a control. Peptide affinities for each of three binding sites [GACC, GCAC, and GCGC (wild type)] were determined by quantitatively gel-shift analysis (Table 3) (Example 6). Each of the variant peptides binds with high affinity to the site used for its selection (Table 3, boxed entries). Moreover, the DSNR and QGSR peptides exhibit new specificities in that they bind to these new sites substantially better than they bind to GCGC. The RADR peptide (unlike the QGSR peptide) does not discriminate well between GCAC and GCGC. The only difference in the selection conditions for these two variants was the use of competitor Zif268 site in the selections that yielded QGSR.

TABLE 3

| Finger one Sequence | Apparent $K_d$ (nM) | | |
|---|---|---|---|
| −1 2 3 6 | GACC | GCAC | GCGC (wt) |
| DSNR | 0.019 | 2.5 | 1.8 |
| RADR | 9.3 | 0.068 | 0.035 |
| QGSR | 1.8 | 0.055 | 0.54 |
| RDER (wt) | 33.0 | 5.6 | 2.7 |

Apparent $K_d$'s for the binding of zinc finger peptides to DNA fragments containing the GACC, GCAC, and GCGC (wild type) forms of the Zif268 binding site. Each peptide is specified by the amino acid residues at the four positions of finger one that were randomized in the library (−1, 2, 3, and 6). RDER is wild type. The three DNA duplexes share the sequence (SEQ ID NO 5) and are specified by the bases at the positions of four X's. [The bracketed region marks the position of the Zif268 binding site GCGTGGGCG (SEQ ID NO:9)] (Pavletich, N. P. and Pabo, C. O., Science, 252:809 (1991)).

The experiments reported herein demonstrate that the phage display system can be used to select zinc fingers with novel DNA-binding specificities. Based on the present disclosure, the skilled artisan will be able to select a wide variety four base pair sequences and engineer zinc fingers which bind specifically to desired four base pair sequences.

Based on the present disclosure, it is possible to construct a multifingered protein in which more than one finger has each been selected to bind to a specific subsite. As a result, a multifingered protein can be engineered such that each finger binds to an adjacent and overlapping subsite. For example, a three-fingered protein can be engineered to bind to the underlined target in the HIV promoter site: ATGCT-GCATATAAGCAGCTGCTT (SEQ. ID NO 6). The underlined target contains three overlapping subsites (CTGC, CATA and ATAA). A zinc finger phage library is prepared as in Examples 1–3. DNA for selection by zinc finger phage is then prepared by substituting XXXX in FIG. 3 with one of the overlapping subsites, for example CTGC. Zinc finger phage is then selected for binding to the selection DNA, as in Example 4, to obtain a pool of phages expressing zinc fingers specific for CTGC. The DNA coding for the zinc fingers which bind CTGC are then amplified by polymerase chain reaction to give a first pool of finger genes. This process is repeated for the other two subsites to give a second and third pool of finger genes. The three pools are then used to construct a new phage vector in which each of three zinc fingers have been selected for binding to the adjacent and overlapping subsite (i.e. the first finger will contact ATAA, the second finger will contact CATA, and the third finger will contact CTGC). Phages expressing this new library will then be selected for binding to the HIV promoter target sequence. A three-fingered protein will be obtained which binds to the HIV target sequence.

The invention is illustrated by the following examples, which are not to be construed as limiting in any way.

EXAMPLE 1

Construction of the Zif Phage Vector fd-tet-Zif

The phage vector fUSE3 (19) was converted into fd-tet.Zif in two steps: (i) A polylinker was inserted into the Xho I site of fUSE3 and (ii) a PCR-amplified fragment of Zif268 complementary DNA encompassing bases 1287 through 1585 (Christy, B. A., et al., *Proc. Natl. Acad. Sci. U.S.A.*, 85:7857 (1988)) was cut with Apa I and Xba I and then ligated into the Apa I and Spe I sites of the polylinker.

EXAMPLE 2

Production of Zif Phage

MC1061 cells (Smith, G. P. and Scott, J. K., *Methods Enzymol.*, 217:228 (1993)) that contained fd-tet.Zif were grown to saturation (room temperature, about 40 hours, no agitation) under anaerobic conditions in 0.05 liter of Zif phage broth [(tryptone (32 g liter$^{-1}$), yeast extract (20 g liter$^{-1}$), glucose (8 g liter$^{-1}$), casamino acids (1 g liter$^{-1}$) tetracycline (0.02 g liter$^{-1}$), thiamine (0.5 mg liter$^{-1}$), 100 µM ZnCl$_2$, 50 µM dithiothreitol, 86 mM NaCl and 40 mM Hepes (pH 7.8)]. To increase titer, cultures were grown in dialysis tubes (50-kD) cutoff) suspended in 1 liter of broth. Phage were titered as tetracycline-transducing units (TTU) essentially as described (Smith, G. P. and Scott, J. K., *Methods Enzymol.*, 217:228 (1993)) except that starved K91 cells had been stored at −80° C. in a buffer containing 67 mM NaCl, 42 mM NH$_4$H$_2$PO$_4$ and 14% glycerol. Titers of Zif phage cultures were 0.5×10⁹ to 14×10⁹ TTU/ml.

EXAMPLE 3

Construction of the Phage Library

Two oligonucleotides were synthesized: 5-GGAATCGATTCCATGGGGCCCCATGAACGGCC GTACGCCTTGCCCTGTCGAGTCCTGCGATCGT CGATTTTCG (SEQ ID NO. 7) and 5'-CCATCTCGATC GCATGCATA TTCGACACTGGAAGGGCTTCTGGCCT- GTGTGGATCCGGATATGSNNGGTGAGSNNSNNA GASNNCGAAAATCGACG (SEQ ID NO. 8) (N=A, T, G and C; S=G and C), with complementary 12-base 3' ends. These were annealed and then extended with sequenase 2.0 (United States Biochemical). The resulting duplex was digested with Apa I and Sph I (sites are underlined) and ligated with the large Apa I-Sph I fragment of fd-tet.Zif. Ligation products were electroporated into MC1061 cells (Smith, G. P. and Scott, J. K., *Methods Enzymol.*, 217:228 (1993)), and this yielded about 2.8×10⁷ independent transformants. This library was grown essentially as described in Example 2. Phage were purified by ultracentrifugation (171, 000 g, 4° C., 6 hours), and phage pellets were resuspended in about 1/100 volume of binding buffer [50 mM NaCl, 5 mM MgCl$_2$, 10 µM ZnCl$_2$, 5% glycerol, bovine serum albumin (BSA; 0.1 mg/ml), and 15 mM Hepes (pH 7.8)]. This final phage library preparation (about 4.7×10¹¹ TTU) was stored anaerobically (<1 ppm O$_2$) on ice. Because of concerns about oxidation, all phage manipulations were done so as to minimize exposure to O$_2$. To estimate library complexity, 20 unselected were sequenced clones. (Single-stranded templates were sequenced with sequenase 2.0 and protocols from United States Biochemical). Three corresponded to the parent construct (fd-tet.Zif) and appear to have resulted from the reinsertion of the fragment excised during library construction. Seventeen phage contained the correct library insert, but there was a significant cytosine bias at the randomized codons. Base ratios were C:A:T:G= 48:19:19:15 at the first two codon positions and C:G=74:6 at position 3.

EXAMPLE 4

Selection Protocol for Phage which Recognize Altered Binding Sites

The selection protocol is based on the "biopanning" procedure (Smith, G. P. and Scott, J. K., *Methods Enzymol.*, 217:228 (1993)). The first round in each initial selection series (the leftmost arrow in each of the three pathways in FIG. 4) was done as follows: Binding reactions (121 µl) were made that contained about 3.5×10¹⁰ TTU of library phage, 39 nM of biotinylated target DNA [GACC, GCAC, or CCTG (FIG. 3)], and sheared calf thymus DNA (0.059 mg/ml) in 0.9× binding buffer (see Example 3). Each sample was preincubated for 50 minutes, diluted into 3.6 volumes of 0.05 M NaCl wash buffer [0.05 M NaCl with 5 MM MgCl$_2$, 10 µM ZnCl$_2$, 5% glycerol, 0.5% w/v Triton X-100, and 15 mM Hepes (pH 7.8)], and applied to streptavidin-coated wells (six wells, 30 µl per well) of a Pro-Bind plate (Becton Dickinson). After 50 minutes the samples were removed from the wells and then (i) over a period of 35 minutes, the wells were rinsed 10 times with 0.25 ml of 0.45M NaCl wash buffer (identical to 0.05M NaCl wash buffer except for the higher NaCl concentration) and (ii) 40 µl of elution buffer [binding buffer (see Example 3) with 4M NaCl] was added to each well. After eluting for 2 hours, each set of six eluates was pooled, titered, and used to infect K91 cells (see Example 2). Transduced cells were incubated for 1 hour at 37° C. in 5 ml of LB broth containing tetracycline (0.2 µg/ml), centrifuged (15 minutes, 1600 g), and resuspended in 50 ml of degassed Zif phage broth. Each culture then grown anaerobically in a 50-ml centrifuged tube and purified essentially as described in Example 3. Other rounds of selection in the initial series were similar except that, starting at round 3, sonicated salmon sperm DNA was substituted for sheared calf thymus DNA in the binding reactions. Selections in the later series were similar except that 0.75M NaCl washes were used and the binding reactions in one of the GCAC selection series included a nonbiotinylated Zif268 binding site (0.36 µM) as a specific competitor. All phage manipulations, except for elution and infection of K91 cells, were carried our in an anaerobic chamber with less than 1 ppm of O$_2$.

In the first round of selection, <0.009% of library phage applied to the streptavidin-coated wells was recovered in the eluates. By the fifth round this retention efficiency had risen to 0.6 to 0.8% for the GACC and GCAC phage pools, but was less than 0.001% for the CCTG pool. For comparison, control experiments using Zif phage and a biotinylated wild-type Zif site typically yielded etention efficiencies of 0.5 to 1.0%.

EXAMPLE 5

Purification of Zinc Finger Variants

The zinc finger regions from the phage variants [corresponding to residues 333 to 421 of Zif268 (Christy, B. A., et al., *Proc. Natl. Acad. Sci. U.S.A.*, 85:7857 (1988))] were subcloned into the T7 expression vectors pET-3d or pET-21d (Novagen). These expression constructs were transformed into BL21 cells containing the pLysS plasmid and then induced as recommended (Novagen). Additionally, the corresponding wild-type peptide (RDER) was expressed as described (Pavletich, N. P. and Pabo, C. O., *Science*, 252:809 (1991)). Zinc finger peptides were purified by reversed-phase batch extraction and reversed phase high-performance liquid chromatography (Pavletich, N. P. and Pabo, C. O., *Science*, 252:809 (1991)). The final peptide preparations were reconstituted in water in an anaerobic chamber and adjusted to 2.75 mM ZnSO$_4$ and 50 mM bis-tris propane (pH 6.8). Peptide samples were stored at −80° C. To estimate purity, peptides were subjected to SDS-polyacrylamide gel electrophoresis and silver staining. No impurities staining as intensely as 2% of the purified peptide were observed in any preparation (12).

EXAMPLE 6

Derivation of Binding Constant

To derive apparent dissociation constants ($K_d$'s) (i) quantitative gel-shift analysis was used to determine the fraction of DNA fragment bound at a series of peptide concentrations, (ii) the $K_d$ was estimated at each point in the transition region of the resulting "binding curve," and (iii) these $K_d$'s were averaged. Those points were used for which $0.1 \leq$ fraction DNA bound $\leq 0.9$ (six or seven points). Standard deviations were always $<K_d$ (average)/4. Binding reactions contained radioactive DNA fragment (about 2.5 pM or about 25 pM), peptide (from a twofold dilution series), and poly (dI-dC)-poly (dI-dC) (14.7 µg/ml; Pharmacia) in degassed gel-shift buffer [50 mM NaCl, 5 mM MgCl$_2$, 10 µM ZnSO$_4$, 5% glycerol, BSA (0.1 mg/ml), 0.1% NP-40, and 15 mM Hepes (pH 7.8)]. Binding reactions were equilibrated at room temperature for either 30 minutes (for RDER) or 4 hours (for the variant peptides) and electrophoresed on 10% poly-acrylamide gels in 0.03M tris-Hepes (pH 7.8). (Control experiments showed that the variant peptides required longer equilibration times). Dried gels were quantitated with the use of a Phosphorimager system (Molecular Dynamics). A freshly thawed sample of peptide was used for each set of gel-shift experiments, and the binding activity was determined by titrating a portion of each sample against a defined concentration of binding site (150 µM or 300 µM). Each sample was titrated twice, with two different DNA fragments (of the three in Table 3), and the calculated activities always agreed within 20%.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

---

What is claimed is:

1. A polypeptide comprising three zinc fingers, each of said zinc fingers comprising a set of base-contacting amino acid residues, wherein:

a) at least one set of base-contacting amino acid residues in at least one zinc finger differs in sequence at one or more base-contacting amino acid residues as compared with a corresponding set of base-contacting amino acid residues in any known wild type zinc finger protein;

b) the polypeptide has a DNA base sequence specificity different from that of any known wild type zinc finger protein; and c) the polypeptide binds a targeted polynucleotide with a dissociation constant of less than about 1.0 nanomolar.

2. The polypeptide of claim 1 wherein the three or more zing fingers bind the targeted polynucleotide with an dissociation constant of less than about 0.5 nanomolar.

3. The polypeptide of claim 2 wherein the wild type zinc finger is selected from the group consisting of EGR1, EGR2, GLI, Wilm's tumor gene, Sp1, Hunchback, Kruppel, ADR1 and BrLA.

4. The polypeptide of claim 1 wherein the targeted polynucleotide is an HIV promoter.

5. The polypeptide of claim 1 wherein the amino acids at positions 3 and 6 of at least one zinc finger are asparagine and arginine, respectively, wherein the amino acid at position −1 is selected from the group consisting of serine, threonine and aspartic acid and wherein the targeted polynucleotide comprises GACC.

6. The polypeptide of claim 1 wherein the amino acids at positions −1, 3 and 6 of at least one zinc finger are arginine, aspartic acid and arginine, respectively, and the targeted polynucleotide comprises GCAC.

7. The polypeptide of claim 1 wherein the amino acids at positions 2 and 6 of at least one zinc finger are glycine and arginine, respectively, and wherein the amino acid at position 3 is serine or threonine and wherein the targeted polynucleotide comprises GCAC.

8. A polypeptide comprising three zinc fingers, wherein the polypeptide a) has essentially the same amino acid sequence as a wild type zinc finger protein, further characterized by at least one or more point mutations at one or more base-contacting amino acid residues;

b) has a base sequence specificity different from the wild type zinc finger protein; and c) binds a targeted polynucleotide with a dissociation constant of less than about 1.0 nanomolar.

* * * * *